United States Patent [19]
Vignaud et al.

[11] Patent Number: 5,290,288
[45] Date of Patent: Mar. 1, 1994

[54] MULTI-FUNCTION DEVICE FOR THE OSTEOSYNTHESIS OF RACHIS

[76] Inventors: Jean-Louis Vignaud, 10 impasse Francois Audouin, F-33400 Talence, France; Patrick Henry, 19 avenue de la République, F-92400 Courbevoie, France

[21] Appl. No.: 768,529
[22] PCT Filed: Feb. 8, 1991
[86] PCT No.: PCT/FR91/00099
§ 371 Date: Oct. 4, 1991
§ 102(e) Date: Oct. 4, 1991
[87] PCT Pub. No.: WO91/11967
PCT Pub. Date: Aug. 22, 1991
[51] Int. Cl.$^5$ .................................. A61B 17/56
[52] U.S. Cl. ............................ 606/61; 606/69; 606/73
[58] Field of Search ............ 606/65, 72, 73, 75, 606/69, 70, 71, 67, 68, 60, 61, 62, 57, 59; 623/17

[56] References Cited

U.S. PATENT DOCUMENTS

| | | | |
|---|---|---|---|
| 1,390,485 | 9/1921 | Bell | 606/72 |
| 2,077,804 | 4/1937 | Morrison | 606/72 |
| 3,067,740 | 12/1962 | Haboush | 606/72 |
| 4,456,005 | 6/1984 | Lichty | 606/73 |
| 4,648,388 | 3/1987 | Steffer | 606/73 |
| 4,658,809 | 4/1987 | Ulrich | 606/73 |
| 4,696,290 | 9/1987 | Steffee | 606/73 |
| 4,946,458 | 8/1990 | Harms | 606/72 |
| 4,963,144 | 10/1990 | Huene | 606/73 |
| 5,085,660 | 2/1992 | Lin | 606/72 |

FOREIGN PATENT DOCUMENTS

| | | | |
|---|---|---|---|
| 0241914 | 10/1989 | European Pat. Off. | |
| 0408489 | 1/1991 | European Pat. Off. | 606/72 |
| 2615095 | 11/1988 | France | |
| 0780652 | 8/1957 | United Kingdom | |

*Primary Examiner*—Michael A. Brown
*Attorney, Agent, or Firm*—Roylance, Abrams, Berdo & Goodman

[57] ABSTRACT

The object of the invention is a device for the osteosynthesis of rachis having pedicular screws, of the type that comprises a threaded, ogival-shaped point (1) and a threaded head (3) that are separated by a hexagonal body (2), said screws being linked by a connection member (5,6) characterized in that it also comprises a sole fixing part (7,8) provided with a passage hole (9) for said threaded head on which a nut (4,4') is screwed for locking the assembly consisting of the fixing part (7,8) and the connection member (5,6) on said head (3), one of these, either the fixing part or the connection member having its inner face shaped in order to provide a groove (17,21) for the accomodation and locking against rotation of said hexagonal body (2).

8 Claims, 1 Drawing Sheet

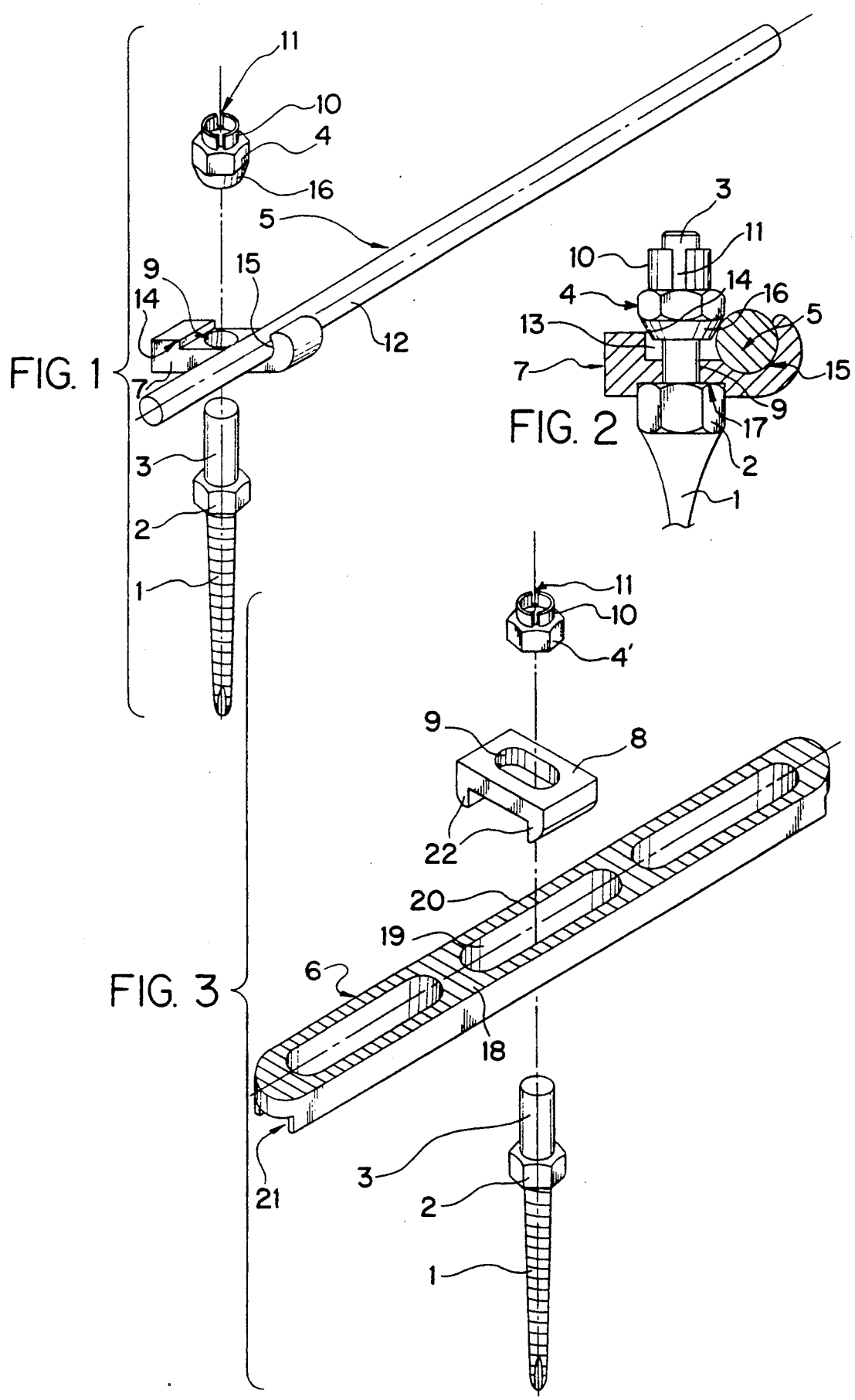

MULTI-FUNCTION DEVICE FOR THE OSTEOSYNTHESIS OF RACHIS

This invention is relative to a device permitting an osteosynthesis of rachis from the rear by means of implants, a portion of which is intended for bone anchorage in vertebral pedicles and another portion is intended to accommodate either a plate or a rod in order to connect the screws together.

As a rule, pedicular screws are implanted, that are connected solely either through plates or through rods.

The purpose of the invention is to provide an instrument of simple design, permitting a specially accurate and reliable positioning and locking of a plate as well as a rod, in order to facilitate the osteosynthesis of rachis, regardless of the anatomical conditions and deformations caused by kyphosis, scoliosis or scolio-kyphosis.

To this purpose, one object of the invention is a device for rachis osteosynthesis with pedicular screws of the type comprising an ogival-shaped threaded point and a threaded head, that are separated by a hexagonal body, said screws being connected by a connection member, characterised in that it also has one fixing part provided with a hole for the passage of said threaded head on which a locking nut is screwed for the assembly consisting of the fixing part and the connection member on said head, one of either the fixing part or the connecting member being shaped on its inner face in order to provide a groove to accommodate said hexagonal body and locking it against rotation, said part, in form of a U-shaped part, being also striated on its face opposing the plate.

According to an application of the device, more particularly to the fixing of a rod, the device is characterized in that said fixing part comprises, at its upper face, a groove in the bottom of which said hole is provided, one flank of which forms a shoulder, whereas the other flank defines a concave-shaped surface for the accommodation of said rod, said locking nut being provided ats lower face with a truncated portion capable of abutting against said shoulder on the one hand, and against said rod on the other hand and in that the lower face of said fixing part comprises said groove for accommodating and locking the hexagonal body.

According to an application of the device, more particularly to the fixing of a plate, the device is characterized in that said fixing part is a U-shaped part overlapping the upper face of said plate provided with said passage hole and flanked by two lateral parallel protusions, in that said plate comprises oval-shaped holes and is provided with transversal striae on its upper face and with said accommodation and locking groove for the hexagonal body on its lower face.

FIG. 1 of the drawing is an exploded view of an embodiment of the device of the invention for fixing a rod, FIG. 2 is a cross section view of the device of FIG. 2 in an assembled condition, FIG. 3 is an exploded view of an embodiment of the device for fixing a plate, The device of the invention comprises pedicular screws of a known general type, consisting of three parts: a point 1, a body 2, a head 3.

The screw is made from materials approved for surgical uses in order to be bio-compatible and to eliminate any breaks of the materials when it enters the vertebral body.

The screw point 1 is threaded and ogival-shaped and it is advantageous that the conicity of thread bottom and thread top is different.

The head of the screw 3 is cylindrical-shaped with a threading compatible for a locking nut (4,4′) for either a rod 5 (FIG. 1) or a plate 6 (FIG. 3) by means of one auxiliary part (7 or 8) provided with a smooth hole 9 at its central portion and threaded onto the head 3.

Nuts (4,4′) have an extension at their top in form of a cylindrical tubular part 10 provided with slots 11 permitting the nuts to be locked whereas the opposing parts 10 are slightly moved closer to each other by means of a plier prior to the insertion of the screw head 3 into the auxiliary part 7,8.

Besides, means are provided on either the sole auxiliary part or the connecting member for pedicular screws, in order to provide a seat for accommodation of and a locking means against rotation of the body 2 of screws with respect to said connecting member.

In the embodiment illustrated in FIGS. 1 and 2, the auxiliary or sole intermediary part 7 is interposed between a rod 5 featuring a cylindrical section of a diameter adequate to withstand the rachis stresses and efforts, whereas the smooth surface has the advantage to permit a flexion in order to achieve a bending to some extent, to match the distorsions or the anatomy of rachis.

At its upper face, the part 7 comprises a central groove 13 in the bottom of which there is a hole 9. One of the flanks of groove 13 is straight and forms a shoulder 14 and the other groove flank defines a concave-shaped surface 15 housing the rod 5 by the hole 9.

In this embodiment, nuts 4 are extended at their lower portion by a truncated portion 16 capable of abutting (FIG. 2) on the one hand, on the edge of shoulder 14, and on the other hand, on rod 5 located in its housing 15 when the assembly 7, 5 is fixed and locked on a screw head 3.

At its lower part, the part is provided with a groove 17 (FIG. 2) associated to the body 2 and accommodating it while simultaneously locking it against rotation.

In the embodiment of FIG. 3, the sole intermediary part 8 is generally shaped as a U-part designed to overlap a sacrolumbar plate 18, with prebend and rectangular cross section, and comprising here and there oval-shaped holes 19 for accommodating the heads of screws 3.

The upper face of plate 18 is provided with transversal striae 20, and the lower face is provided with a groove 21 similar to the groove 17 of the part 7, and designed to accommodate and lock the bodies of screws 2.

The intermediary part 8 has a central portion featuring a hole 9, preferably oval-shaped for easier introduction of the screw head 3 and flanked by two lateral protusions 22 for guiding and wedging the part 8 along the upper striated face of plate 18, whereas the face of part 8 opposing striae 20 features matching striae.

Striae eliminate the need to move screw head 3 in the oval-shaped hole 19, once the nut 4′ is clamped.

Nut 4′ is similar to that shown in FIGS. 1 and 2, except that it has no truncated portion at its base.

By altering the screw sizes (1, 2, 3), the device of the invention makes it possible, in whatever embodiment, to achieve vertebral stabilizations on all the height of the dorsal sacrolumbar rachis.

We claim:

1. A device for osteosynthesis of rachis, comprising:

a first pedicular screw having a threaded, ogival-shaped point and a threaded head separated by a hexagonal body;

a connection member linking said first screw to other screws, said connection member being an elongated plate with elongated openings spaced along said plate for receiving said threaded head, transversal striae being provided on an upper surface of said plate;

a single, one piece fixing part provided with at least one passage hole for receiving said threaded head, said fixing part being a U-shaped part overlying the upper face of said plate and being flanked by two parallel lateral protrusions, striae being provided on a lower surface of said fixing part opposing said plate; and a nut threaded on said threaded head for locking said fixing part and said connection member on said threaded head, said plate having a lower surface shaped to provide a lower groove for receiving and locking said hexagonal body.

2. A device according to claim 1 wherein said passage hole in said fixing part is elongated.

3. A device according to claim 1 wherein said nut has an extension at an upper part thereof in the form of a cylindrical tubular portion split diametrally for nut locking.

4. A device according to claim 1 wherein said lower groove is non-circular in transverse cross section, and is defined, at least in part, by planar surfaces abutting planar surfaces of said hexagonal body.

5. A device for osteosynthesis of rachis, comprising:

pedicular screws having threaded, ogival-shaped points and threaded heads separated by hexagonal bodies;

a connection member linking said screws, said connection member being an elongated plate with elongated openings spaced along said plate for receiving said threaded heads and with a lower groove in a lower surface of said plate for receiving and locking said hexagonal bodies, said lower groove being non-circular in transverse cross section and being defined, at least in part, by planar surfaces abutting planar surfaces of said hexagonal bodies, transversal striae being provided on an upper surface of said plate;

fixing parts provided with passage holes for receiving said threaded heads, said fixing parts being U-shaped parts overlying the upper surface of said plate, each said fixing part being flanked by two lateral protrusions, striae being provided on a lower surface of said fixing parts opposing said plate; and nuts threaded on said threaded heads for locking said fixing parts and said connection member on said threaded heads.

6. A device according to claim 5 wherein said passage holes in said fixing parts are elongated.

7. A device according to claim 5 wherein said nuts have extensions at upper parts thereof in the form of cylindrical tubular portions split diametrally for nut locking.

8. A device according to claim 5 wherein said planar surfaces of said lower groove are parallel.

* * * * *

UNITED STATES PATENT AND TRADEMARK OFFICE
CERTIFICATE OF CORRECTION

PATENT NO. : 5,290,288

DATED : March 1, 1994

INVENTOR(S) : Jean-Louis Vignaud and Patrick Henry

It is certified that error appears in the above-identified patent and that said Letters Patent is hereby corrected as shown below:

On the title page, after

"[87] PCT Pub. No. WO91/11967
    PCT Pub. Date: Aug. 22, 1991"

the following should be added:

-- [30] Foreign Application Priority Data
    Feb. 8, 1990 [FR] France ........... 90 01633 --.

Signed and Sealed this

Twentieth Day of June, 1995

*Attest:*

BRUCE LEHMAN

*Attesting Officer*     Commissioner of Patents and Trademarks